(12) United States Patent
Brandes et al.

(10) Patent No.: US 10,722,727 B2
(45) Date of Patent: Jul. 28, 2020

(54) THERAPEUTIC SIGNAL GENERATOR

(71) Applicant: Bonnie Brandes, Crystal River, FL (US)

(72) Inventors: Bonnie Brandes, Crystal River, FL (US); Paul Esch, Villa Rica, GA (US)

(*) Notice: Subject to any disclaimer, the term of this patent is extended or adjusted under 35 U.S.C. 154(b) by 1093 days.

(21) Appl. No.: 14/901,265

(22) PCT Filed: Jul. 9, 2013

(86) PCT No.: PCT/US2013/049735
§ 371 (c)(1),
(2) Date: Dec. 28, 2015

(87) PCT Pub. No.: WO2015/005908
PCT Pub. Date: Jan. 15, 2015

(65) Prior Publication Data
US 2016/0151641 A1   Jun. 2, 2016

(51) Int. Cl.
*A61N 5/06* (2006.01)
*A61N 2/00* (2006.01)
*A61N 5/067* (2006.01)
*A61H 23/02* (2006.01)
*A61B 18/00* (2006.01)
*A61N 2/02* (2006.01)

(52) U.S. Cl.
CPC .......... *A61N 5/0618* (2013.01); *A61N 2/002* (2013.01); *A61B 2018/00732* (2013.01); *A61H 23/0218* (2013.01); *A61H 23/0236* (2013.01); *A61H 2201/10* (2013.01); *A61H 2201/5005* (2013.01); *A61H 2201/5038* (2013.01); *A61H 2201/5043* (2013.01); *A61N 2/02* (2013.01); *A61N 2005/067* (2013.01); *A61N 2005/0651* (2013.01); *A61N 2005/0659* (2013.01); *A61N 2005/0663* (2013.01)

(58) Field of Classification Search
CPC ................. A61N 5/0618; A61N 2/002; A61N 2005/0659; A61N 2005/067; A61N 2005/0663; A61N 2005/0651; A61N 2/02; A61H 2201/5043; A61H 2201/5038; A61H 2201/5005; A61H 2201/10; A61H 23/0236; A61H 23/0218; A61B 2018/00732

See application file for complete search history.

(56) References Cited

U.S. PATENT DOCUMENTS 4,646,743 A * 3/1987 Parris ...................... A61N 5/06
                                                     250/495.1
4,930,504 A * 6/1990 Diamantopoulos .. A61N 5/0616
                                                     250/494.1

(Continued)

*Primary Examiner* — Gary Jackson
*Assistant Examiner* — Sebastian X Lukjan
(74) *Attorney, Agent, or Firm* — Daniel M. Cohn; Howard M. Cohn

(57) ABSTRACT

An apparatus for generating multiple simultaneous electronic signals is disclosed. The apparatus a signal generator (104), a non-transitory memory (106), a processor (102) configured and disposed to access the non-transitory memory (106), a plurality of laser activation pins (126), a plurality of light emitting diode (LED) activation pins (124). The processor is configured and disposed to activate one or more of the plurality of laser activation pins (126) coordinated to a first output (118) of the signal generator (104).

10 Claims, 10 Drawing Sheets

(56) References Cited

U.S. PATENT DOCUMENTS

| | | | |
|---|---|---|---|
| 5,108,361 A * | 4/1992 | Hein | A61B 5/0482 600/27 |
| 5,445,608 A * | 8/1995 | Chen | A61N 5/0601 604/19 |
| 6,135,995 A | 10/2000 | Arnett et al. | |
| 6,249,698 B1 * | 6/2001 | Parris | A61N 1/322 607/3 |
| 7,161,556 B2 * | 1/2007 | Morgan | H04L 29/12254 340/9.16 |
| 7,402,167 B2 | 7/2008 | Nemenov | |
| 7,833,257 B2 * | 11/2010 | Walsh, Jr. | A61N 5/0603 607/88 |
| 9,352,170 B1 * | 5/2016 | Davis | A61N 5/0618 |
| 2003/0191506 A1 | 10/2003 | Shloznikov | |
| 2007/0167999 A1 * | 7/2007 | Breden | A61N 5/06 607/88 |
| 2008/0065177 A1 * | 3/2008 | Casper | A61N 5/0618 607/88 |
| 2008/0183237 A1 | 7/2008 | Errico et al. | |
| 2009/0088680 A1 * | 4/2009 | Aravanis | A61K 48/005 604/21 |
| 2009/0204175 A1 | 8/2009 | Zanella et al. | |
| 2011/0172747 A1 * | 7/2011 | Weisbart | A61N 5/0613 607/89 |
| 2011/0301515 A1 * | 12/2011 | Lee | A61H 23/0236 601/47 |
| 2011/0311489 A1 * | 12/2011 | Deisseroth | C12N 13/00 424/93.2 |
| 2012/0203055 A1 * | 8/2012 | Pletnev | A61N 2/002 600/14 |
| 2014/0039322 A1 * | 2/2014 | Trujillo | A61B 5/0071 600/476 |
| 2014/0058189 A1 * | 2/2014 | Stubbeman | A61N 2/002 600/13 |
| 2015/0148871 A1 * | 5/2015 | Maxik | H05B 33/0863 607/88 |

\* cited by examiner

THERAPEUTIC SIGNAL GENERATOR

TECHNICAL FIELD OF THE INVENTION

The present invention relates generally to an electronic device for signal generation, and more particularly, to an electronic device for generating signals for therapeutic applications.

BACKGROUND OF THE INVENTION

Primitive reflexes are automatic responses of infants to elements of their environment which are essential for survival. These reflexes, when integrated in the first months of growth, lead to the development of muscle tone, motor skills, sensory integration and cognition. When these primary reflexes remain active and dominant, difficulties emerge. In children who experienced birth brain injuries, these reflexes are never integrated. Additionally, reflexes which were integrated can later re-activate in cases of anoxia (near drowning), brain trauma, toxins, etc. and impede healing as they remain dominant and not integrated.

Primitive reflexes originate in the brain stem, which is the area responsible for survival. The body, under stress, acts from the brain stem and cannot access the prefrontal cortex where information is analyzed. Hence, children and adults with brain assaults can re-activate these reflexes and develop issues of a lack of mobility and function, lack of control of bodily function, speech delay etc.

Frequency therapy is an alternative therapy which takes advantage of the effects of low frequency sound and vibration on human health and wellness. Researchers who have studied the effects of frequency, sound, light, color, and vibration include Royal Rife, as well as many others. Frequency therapy may have the potential to completely transform our heath care schemes. It offers a simple technique to get very detailed holographic information about the body, and has tremendous potential ramifications. It is therefore desirable to have an apparatus to assist in re-integrating these reflexes to facilitate the healing process by applying such therapies.

SUMMARY OF THE INVENTION

In a first aspect, embodiments of the present invention provide an apparatus for generating multiple simultaneous electronic signals, comprising a signal generator, a non-transitory memory, a processor configured and disposed to access the non-transitory memory, a plurality of laser activation pins, a plurality of light emitting diode (LED) activation pins, wherein the processor is configured and disposed to activate one or more of the plurality of laser activation pins coordinated to a first output of the signal generator.

In a second aspect, embodiments of the present invention provide an apparatus for generating multiple simultaneous electronic signals, comprising a signal generator, a non-transitory memory, a processor configured and disposed to access the non-transitory memory, a plurality of laser activation pins, a plurality of light emitting diode (LED) activation pins, wherein the non-transitory memory contains instructions, that when executed by the processor program a plurality of control registers to configure a signal generator to generate a variable frequency pattern on a first output.

In a third aspect, embodiments of the present invention provide an apparatus for generating multiple simultaneous electronic signals, comprising a signal generator, a non-transitory memory, a processor configured and disposed to access the non-transitory memory, a plurality of laser activation pins, a plurality of light emitting diode (LED) activation pins, wherein the non-transitory memory contains instruction, that when executed by the processor program a plurality of control registers to configure a signal generator to generate a first variable frequency pattern on a first output, and a second variable frequency pattern on a second output.

In a fourth aspect, embodiments of the present invention provide a method for generating multiple simultaneous electronic therapeutic signals, comprising: generating a first variable frequency pattern on a first signal output, activating one or more laser activation pins based on an instantaneous state of the variable frequency pattern, and activating one or more light emitting diode (LED) activation pins based on the instantaneous state of the variable frequency pattern.

BRIEF DESCRIPTION OF THE DRAWINGS

The structure, operation, and advantages of the present invention will become further apparent upon consideration of the following description taken in conjunction with the accompanying figures (FIGS.). The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1:
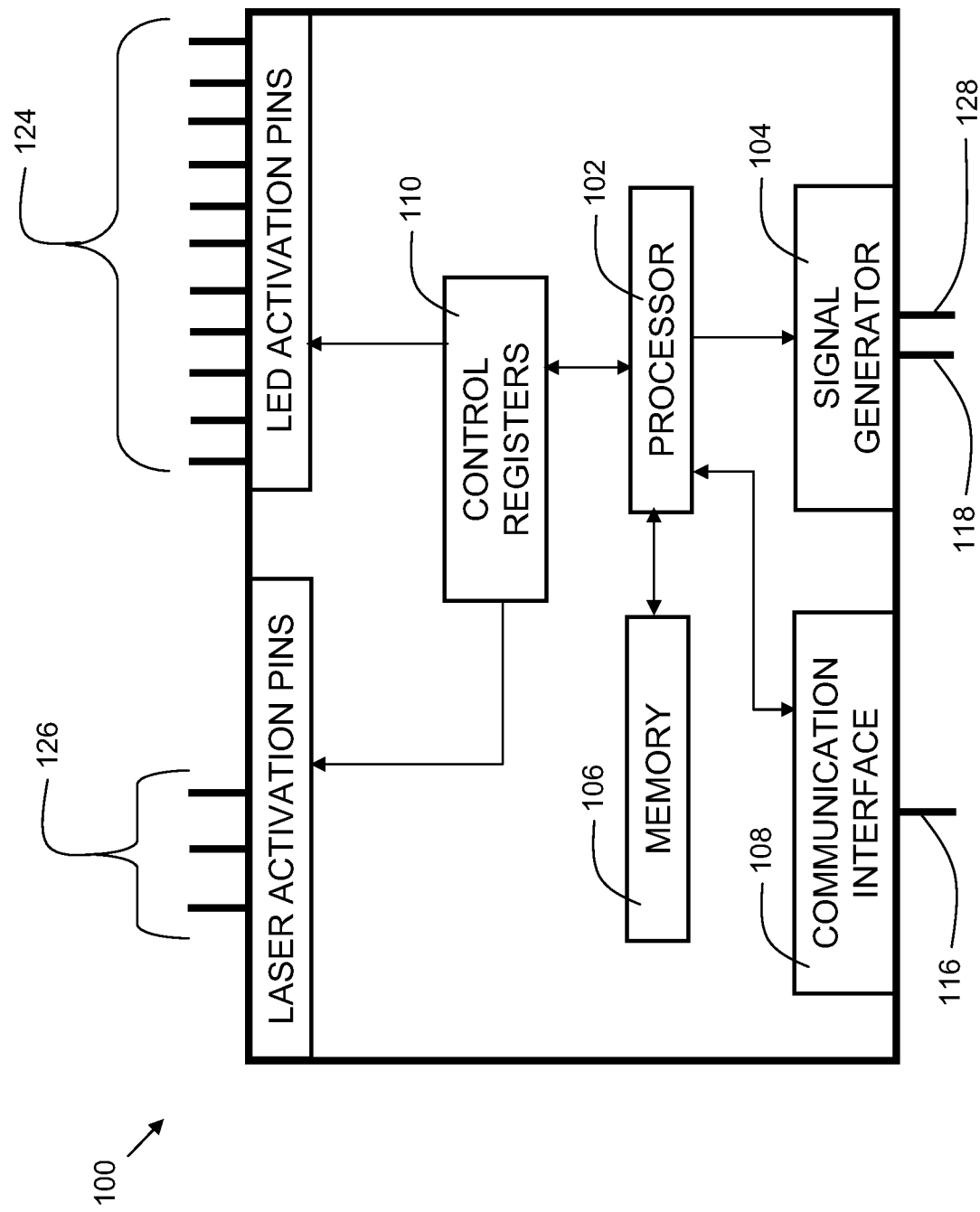

Often, similar elements may be referred to by similar numbers in various figures (FIGs) of the drawing, in which case typically the last two significant digits may be the same, the most significant digit being the number of the drawing figure (FIG). Furthermore, for clarity, some reference numbers may be omitted in certain drawings.

FIG. 1 is a block diagram of an electronic device in accordance with embodiments of the present invention.

Figure 2:
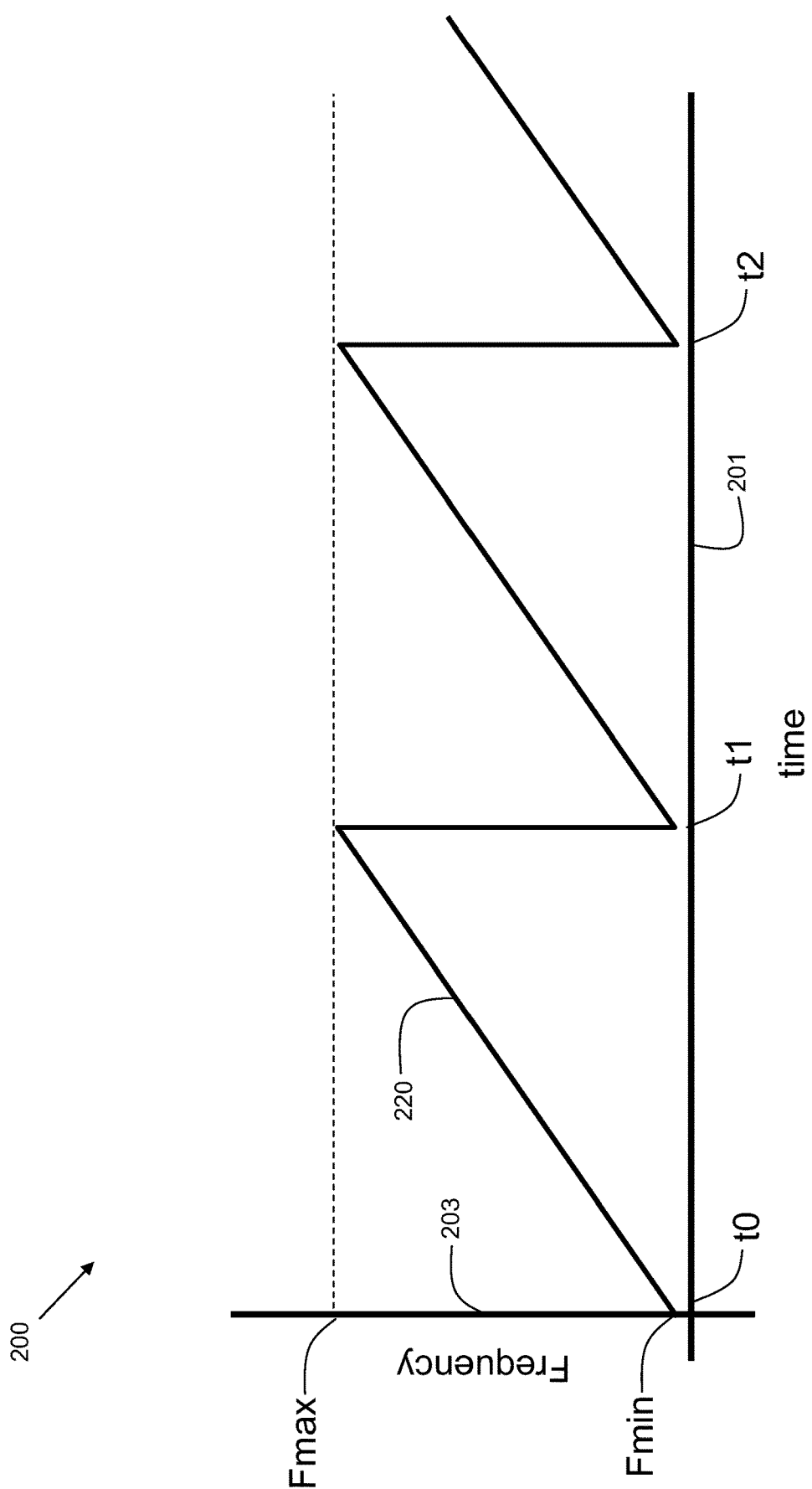

FIG. 2 is a graph illustrating a sweep pattern in accordance with embodiments of the present invention.

Figure 3:
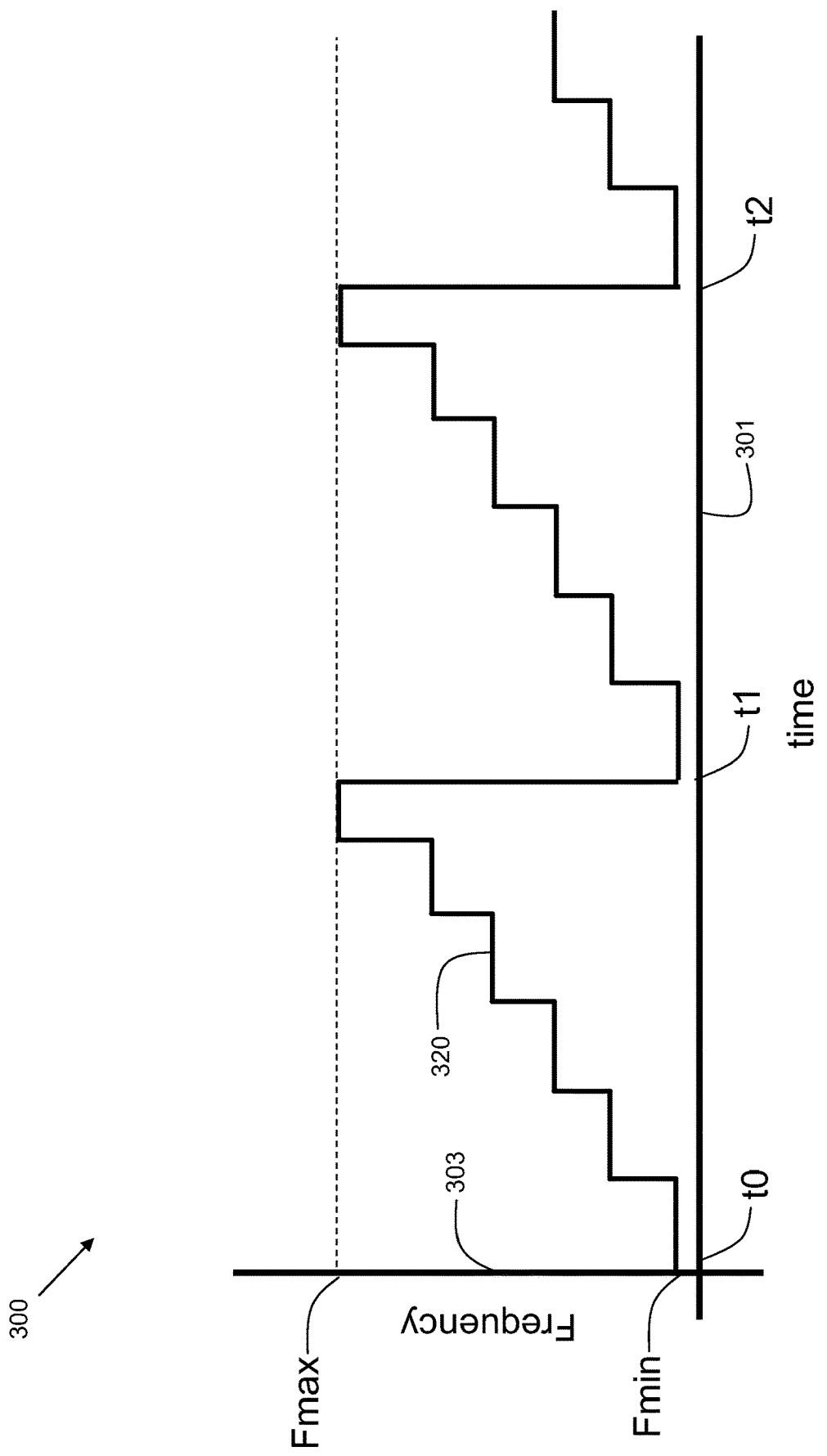

FIG. 3 is a graph illustrating a step pattern in accordance with embodiments of the present invention.

Figure 4:
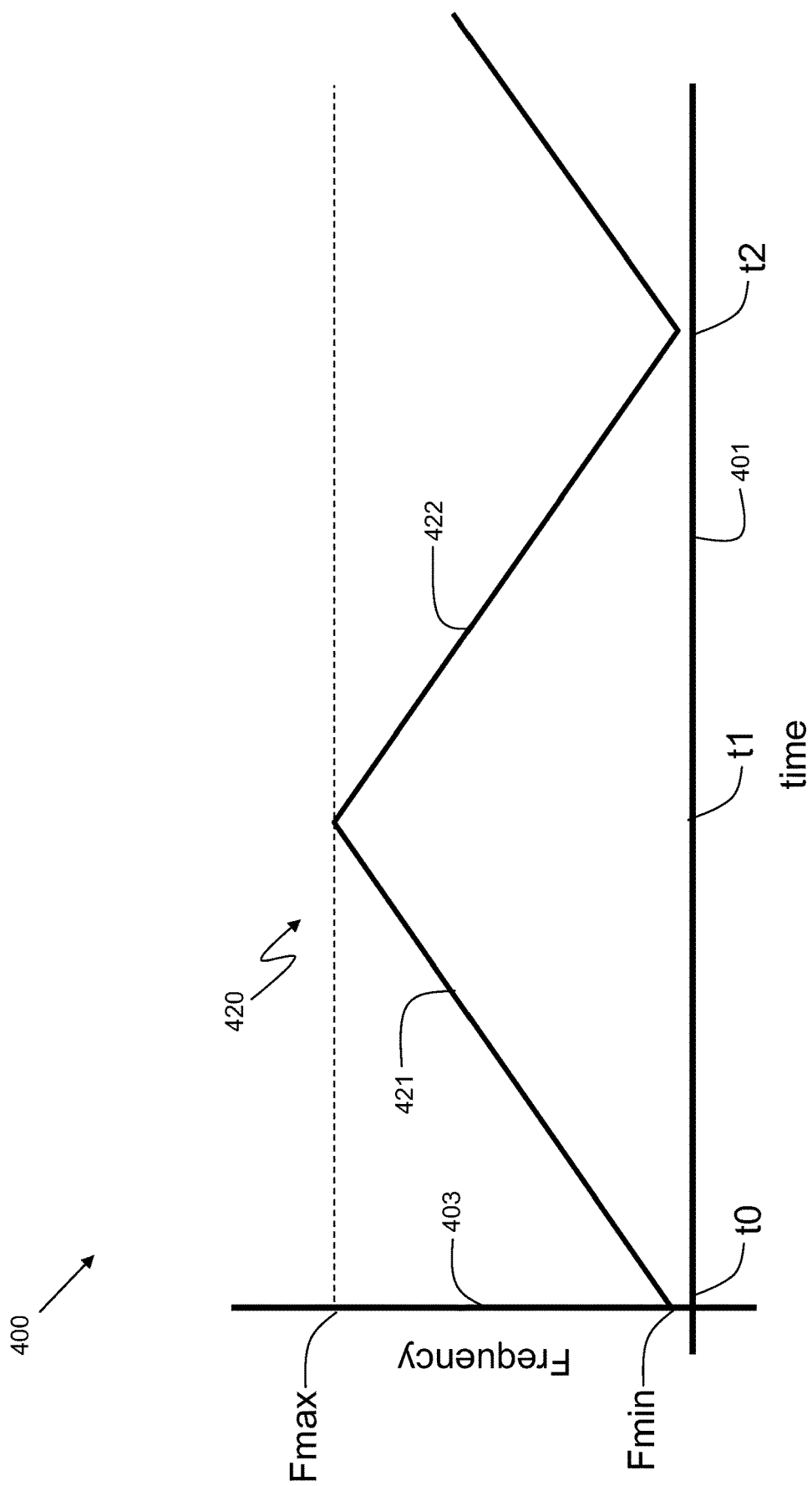

FIG. 4 is a graph illustrating a mirror sweep pattern in accordance with embodiments of the present invention.

Figure 5:
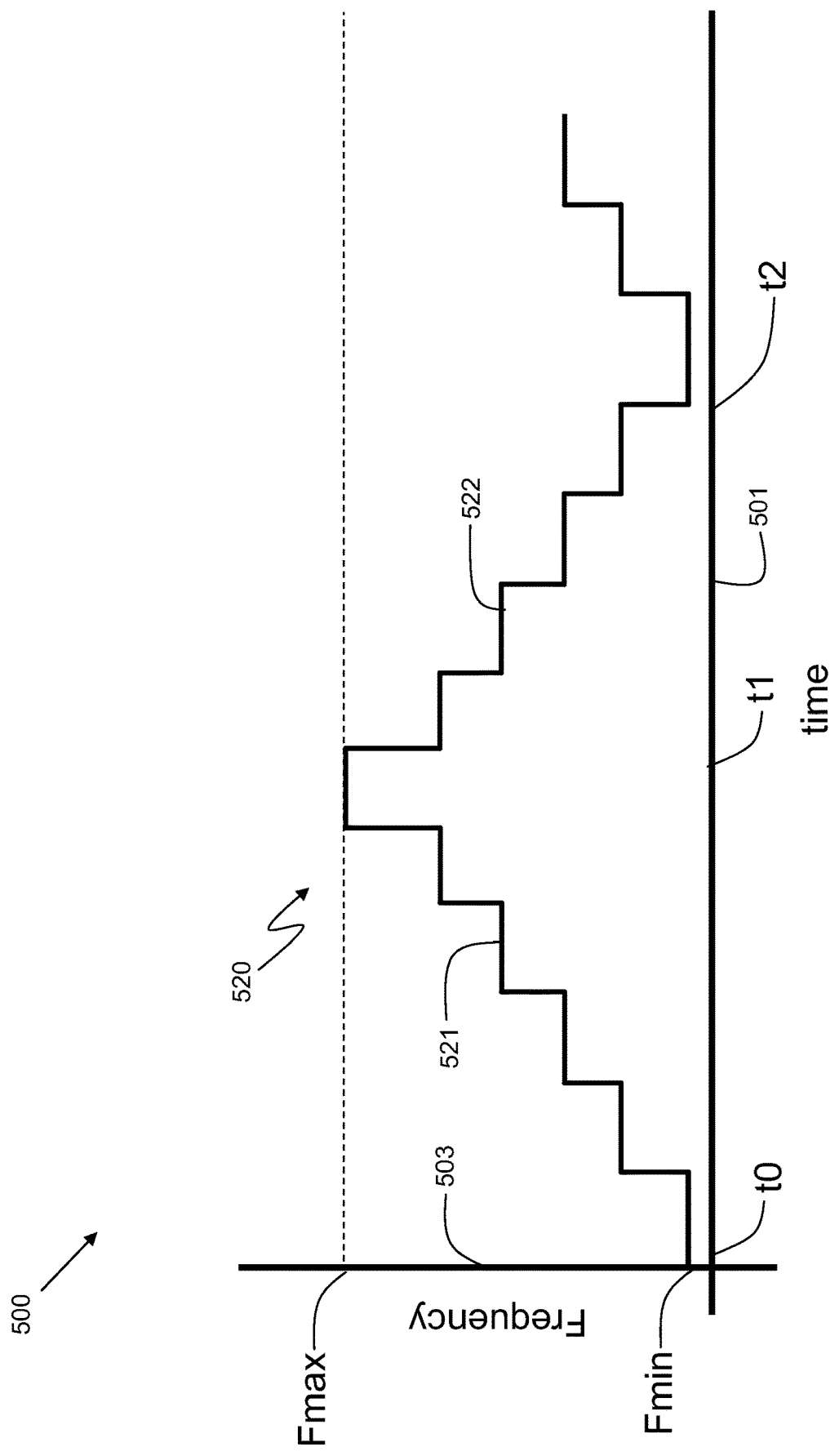

FIG. 5 is a graph illustrating a mirror step pattern in accordance with embodiments of the present invention.

Figure 6:
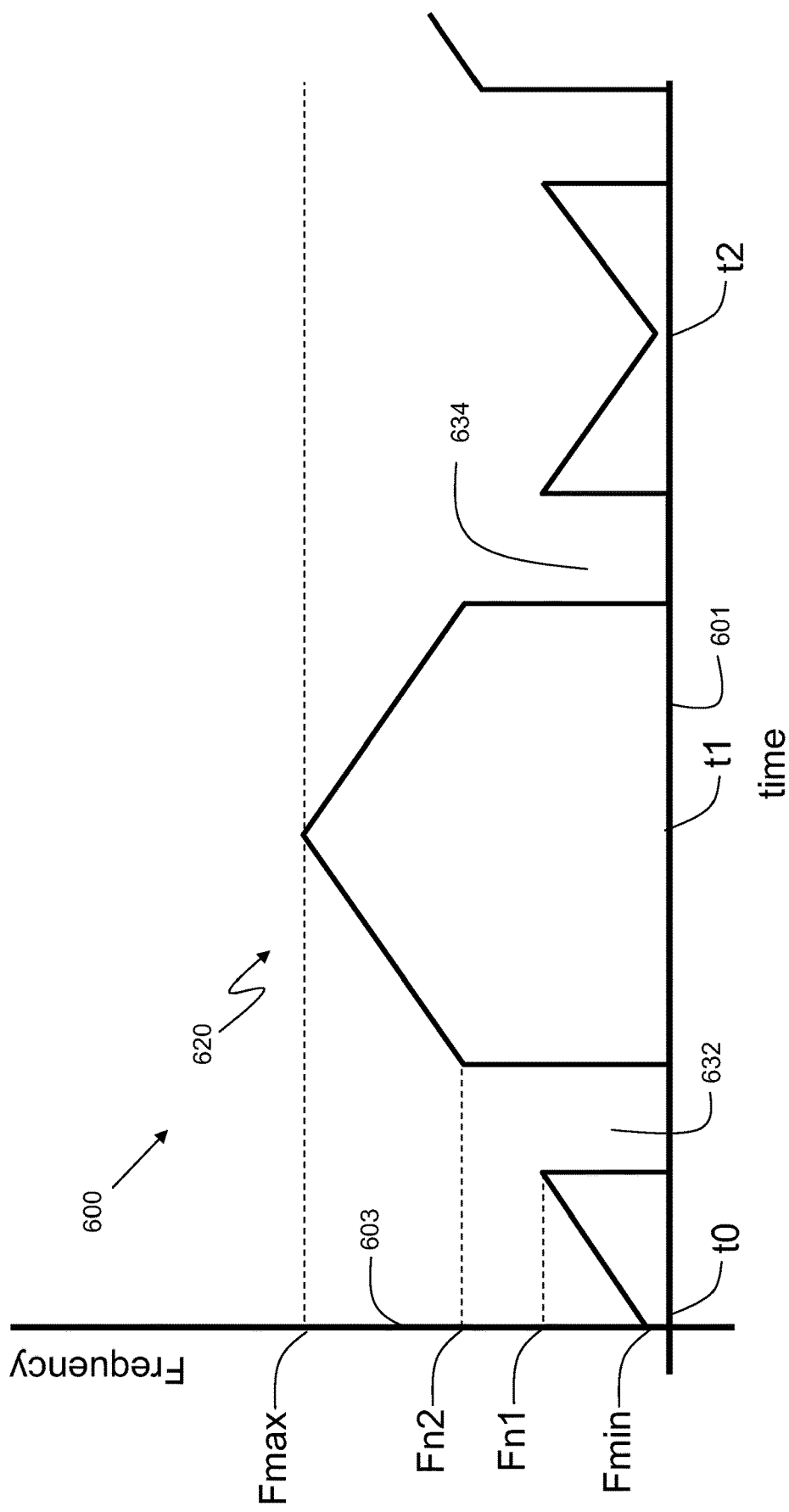

FIG. 6 is a graph illustrating a notched pattern in accordance with embodiments of the present invention.

Figure 7:
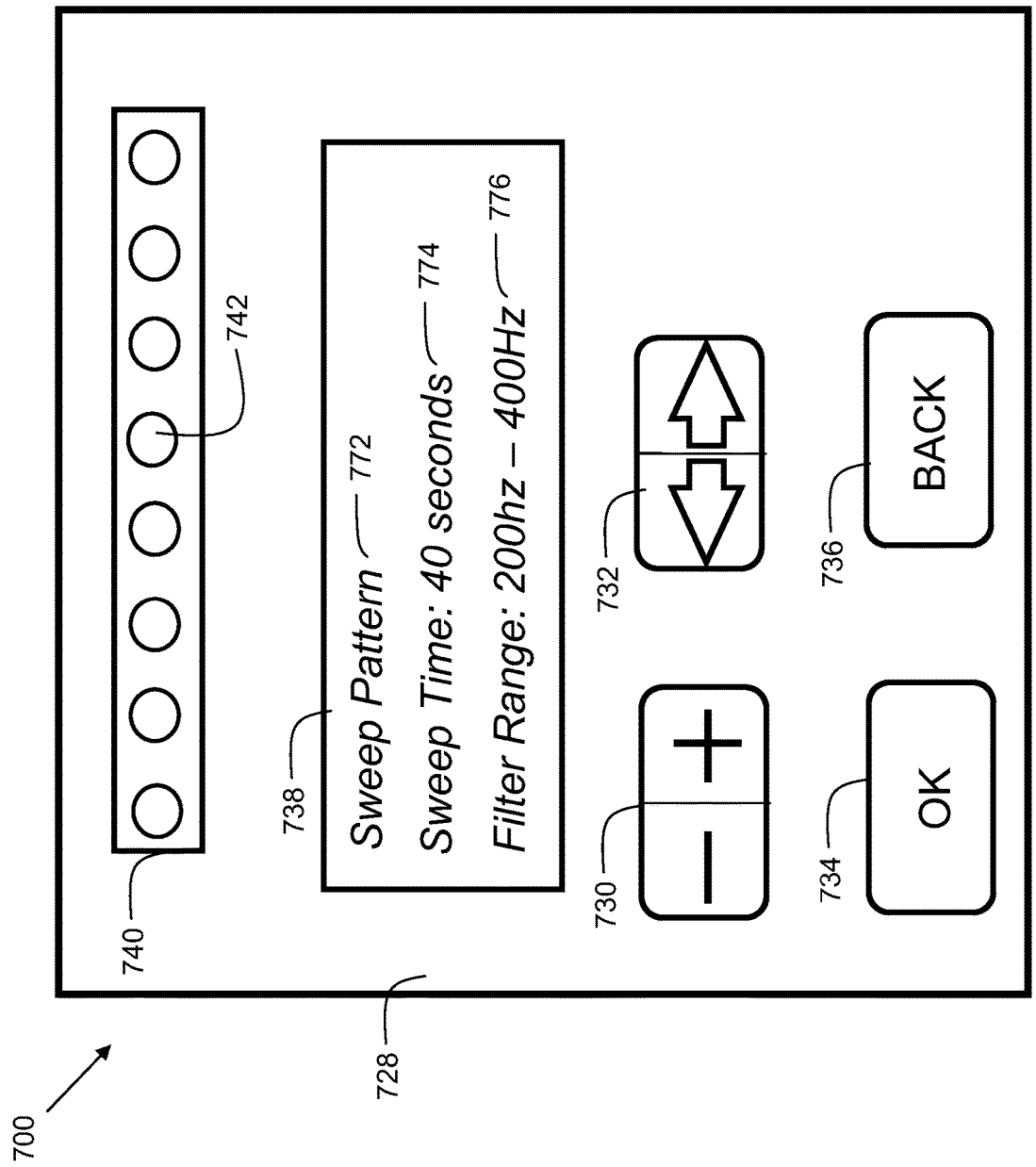

FIG. 7 is an exemplary user interface for an apparatus incorporating an electronic device in accordance with embodiments of the present invention.

Figure 8:
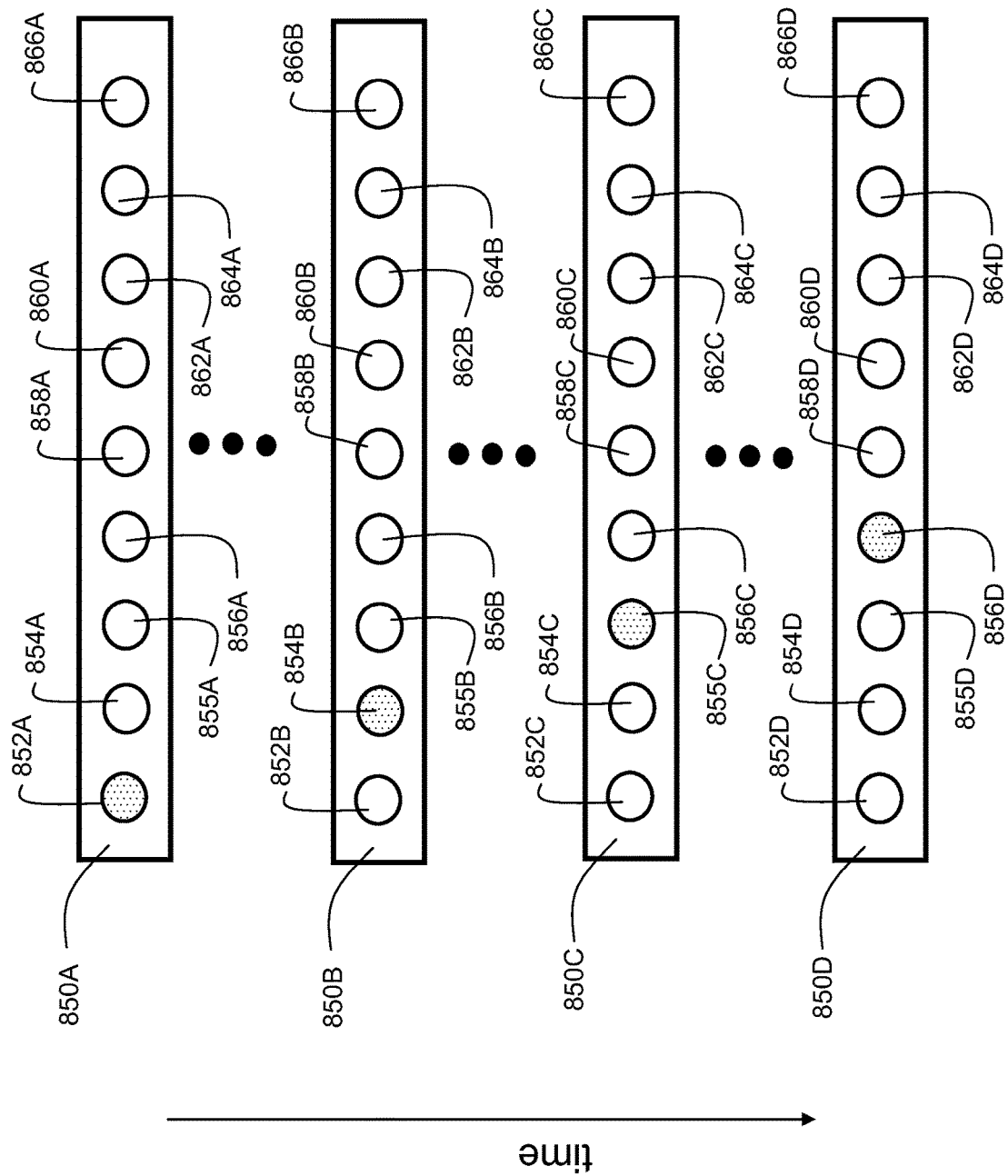

FIG. 8 is an exemplary individual light activation sequence in accordance with embodiments of the present invention.

Figure 9:
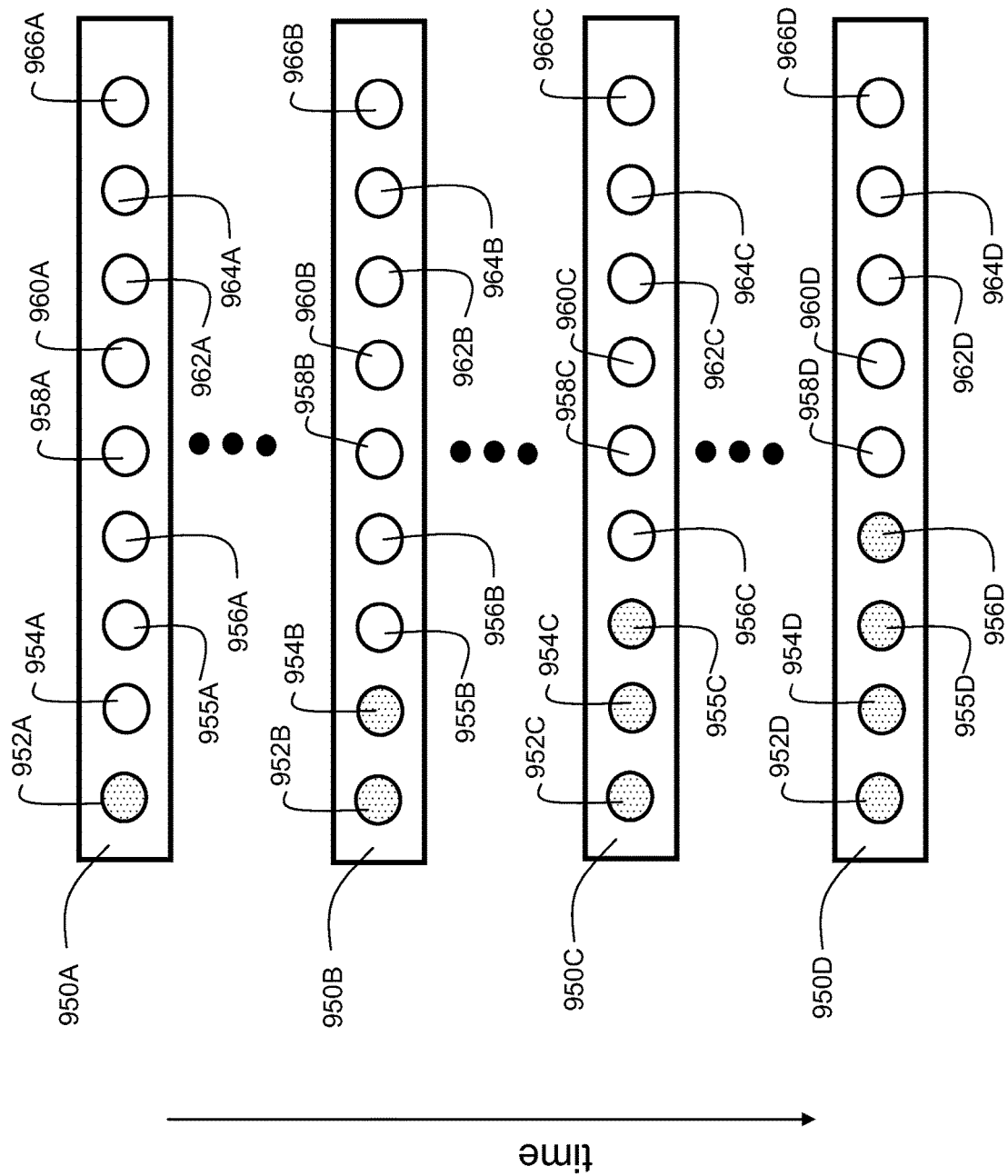

FIG. 9 is an exemplary accumulative light activation sequence in accordance with embodiments of the present invention.

Figure 10:
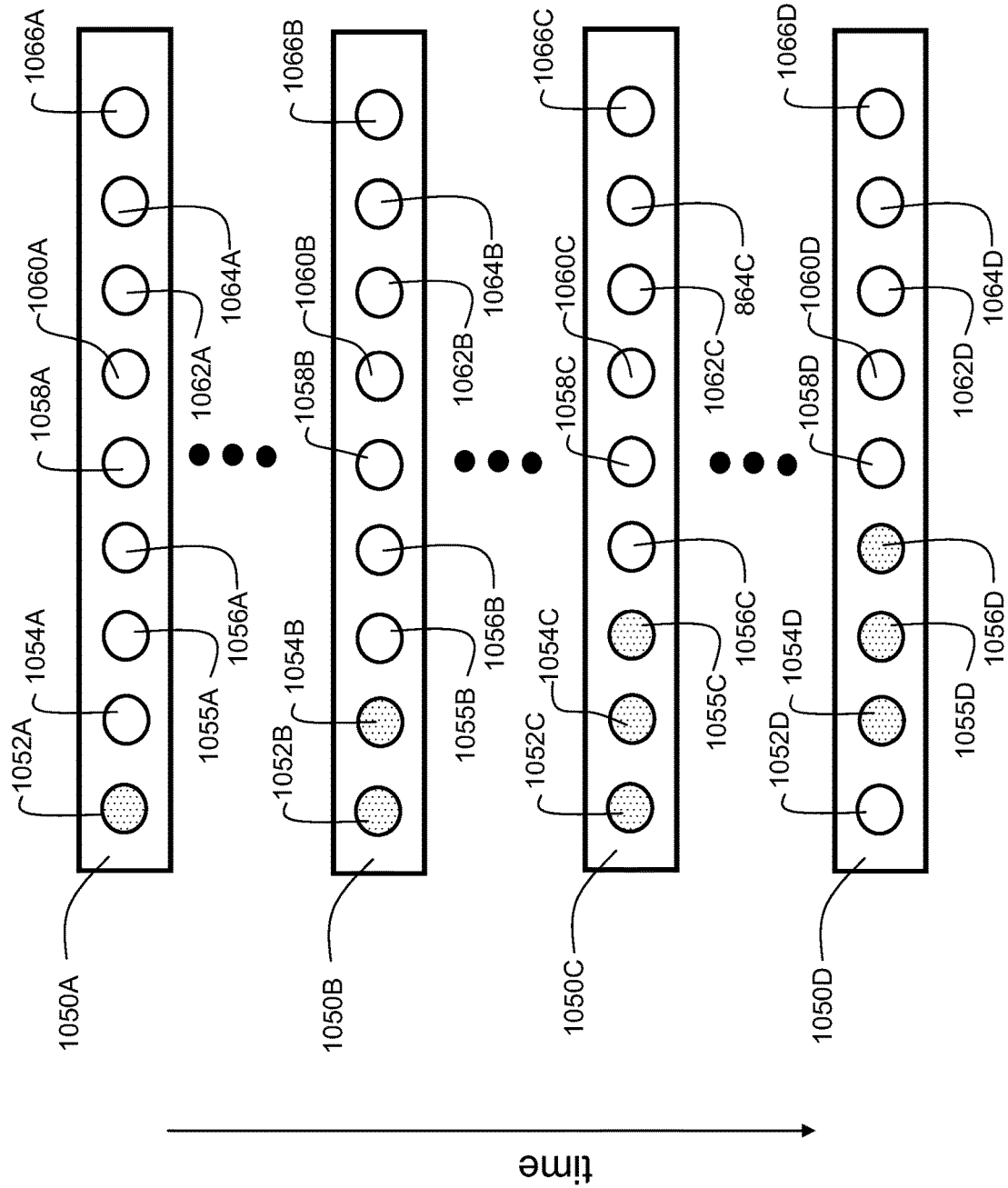

FIG. 10 is an exemplary group light activation sequence in accordance with embodiments of the present invention.

DETAILED DESCRIPTION OF THE INVENTION

Embodiments of the present invention provide an electronic device adapted to generate electronic signals. The electronic signals may comprise variable frequency patterns. Various digital signals may be asserted in a coordinated manner corresponding to the instantaneous state of the varying frequency patterns. In embodiments, the varying frequency patterns may range from about 10 Hz to about 2000 Hz, and may drive transducers such as magnetic coils and/or speakers. The digital signals may be configured to control cold lasers, LEDs, and/or other light sources, including noble gas lights (e.g. neon lights). The combination of the cold lasers, LEDs, and varying frequency patters may be used to administer frequency therapy. The digital signals may include laser activation pins and light emitting diode (LED) activation pins. The laser activation pins and LED activation pins may be activated based on an instantaneous state of the variable frequency patterns. For example, a particular LED activation pin and/or laser activation pin may be activated when the variable frequency pattern is within a certain frequency range. In some embodiments, multiple activation pins may be activated simultaneously along with the variable frequency pattern.

FIG. 1 is a block diagram of an electronic device 100 in accordance with embodiments of the present invention. In some embodiments, electronic device 100 may be a programmable system on a chip (PSoC), and may comprise a processor 102. The processor 102 may be configured to access non-transitory memory 106, which may comprise flash memory, battery-backed SRAM memory, or other suitable non-transitory memory. The processor 102 is configured and disposed to access memory 106 to retrieve instructions that are executed by processor 102 in order to control signal generator 104. Output pins 118 and 128 provide output from the signal generator 104. The signal generator may generate a waveform such as a sine wave, square wave, or sawtooth wave at various frequencies. In some embodiments, the output level may differ on output pin 118 and 128, while the signal output is the same. In this way, a stereo effect may be achieved. For example, in some embodiments, an output signal may "pan" from output pin 118 to output pin 128, to create a stereo effect. Output pins 118 and 128 may be connected to a headphone jack or speaker system. In other embodiments, a temporal delay may be applied to one of the output pins, to create a phase delay effect, such that the signal on output pin 128 is a time-delayed version of the signal on output pin 118. For example, the signal on output pin 118 may be the same as on output pin 128, only delayed by a predetermined time interval (e.g. 200 to 300 milliseconds). In this way a "flanger" effect may be achieved, where the two signals create an interference pattern that provides a plurality of notches and peaks, yielding a distinctive tone. In some embodiments, the signals on output pin 118 may be the same as on output pin 128, and the signal on output pin 118 may be 180 degrees out of phase from the signal on output pin 128. This has applications in Pulsed electromagnetic field therapy (PEMFT), where the signals may be used to drive two electromagnetic coils, such that each coil is 180 degrees out of phase with the other coil.

Communication interface 108 allows data to be exchanged between the processor 102 and external devices via communications input/output signal 116. In some embodiments, the communication input/output signal 116 may include, but is not limited to, I2C, SPI, UART, and USB. The communication interface 108 facilitates a user interface which can be used to adjust parameters to control operation of electronic device 100. Electronic device 100 comprises a plurality of laser activation pins 126 and LED activation pins 124. The laser activation pins 126 and LED activation pins 124 are digital outputs that may be synchronized to a particular output state of signal generator 104. In some embodiments, the laser activation pins 126 may comprise three activation pins. A first laser activation pin may be configured to control a red laser. A second laser activation pin may be configured to control a violet laser. A third laser activation pin may be configured to control an infrared laser.

In some embodiments, the LED activation pins 124 may be configured to control a plurality of light emitting diodes (LEDs). In some embodiments, the LED colors may include red, orange, yellow, green, blue, indigo, violet, and white. Alternatively, another suitable light source, such as small incandescent bulbs, may be used in place of, or in addition to, the light emitting diodes.

A plurality of control registers 110 may be implemented to control various parameters of the electronic device. The control registers may include, but are not limited to, the following registers:

| REGISTER | DESCRIPTION |
| --- | --- |
| PATTERN SELECT | Select between different predefined patterns, such as sweep, step, and mirrored varieties thereof |
| SWEEP TIME | Time period for completing one cycle of a predefined pattern (e.g. in seconds). |
| START FREQUENCY | Starting frequency of the predetermined pattern (e.g. in Hertz) |
| END FREQUENCY | Ending frequency of the predetermined pattern (e.g. in Hertz) |
| NOTCH ACTIVATION | Binary flag to enable the notch filter |
| NOTCH START FREQUENCY | Starting frequency for the notch filter |
| NOTCH END FREQUENCY | Ending frequency for the notch filter |
| LEFT SIGNAL OUTPUT LEVEL | Amplitude control for the left output signal (e.g. 118 of FIG. 1) |
| RIGHT SIGNAL OUTPUT LEVEL | Amplitude control for the right output signal (e.g. 128 of FIG. 1) |
| LEFT SIGNAL DELAY TIME | Applies a delay (e.g. in milliseconds) to the left output signal (e.g. 118 of FIG. 1). |
| RIGHT SIGNAL DELAY TIME | Applies a delay (e.g. in milliseconds) to the right output signal (e.g. 128 of FIG. 1). |
| LED ACTIVATION | Register containing a bit corresponding to each LED activation pin (124 of FIG. 1) |
| LASER ACTIVATION | Register containing a bit corresponding to each laser activation pin (126 of FIG. 1) |

Exemplary use of these registers is described in the following examples of outputs rendered by an electronic device in accordance with exemplary embodiments of the present invention.

FIG. 2 is a graph 200 illustrating a variable frequency pattern sweep pattern in accordance with embodiments of the present invention. The horizontal axis 201 represents time. The vertical axis 203 represents frequency of an output pattern over time. The output pattern 220 starts at a frequency Fmin at time t0, and includes a continuous increase in frequency up to a maximum frequency Fmax at time t1. The process then repeats, up until time t2. The difference between time t1 and time t0 represents the sweep time interval. In some embodiments, the sweep time interval may range from 10 seconds to 100 seconds. In some embodiments, Fmin is 1 Hz and Fmax is 2000 Hz.

FIG. 3 is a graph 300 illustrating a variable frequency pattern step pattern in accordance with embodiments of the present invention. The horizontal axis 301 represents time. The vertical axis 303 represents frequency of an output pattern over time. The output pattern of stepped levels 320 starts at a frequency Fmin at time t0, and includes a stepped increase in frequency up to a maximum frequency Fmax at time t1. While six stepped levels per sweep are shown in FIG. 3, some embodiments may have 8 stepped levels or more. In one embodiment, a first level has a fundamental frequency of 250 Hz, a second level has a fundamental frequency of 500 Hz, a third level has a fundamental frequency of 750 Hz, a fourth level has a fundamental frequency of 1000 Hz, a fifth level has a fundamental frequency of 1250 Hz, a sixth level has a fundamental frequency of 1500 Hz, a seventh level has a fundamental frequency of 1750 Hz, and an eighth level has a fundamental frequency of 2000 Hz. The process then repeats, up until time t2. The difference between time t1 and time t0 represents the sweep time interval. In some embodiments, a different subset of the plurality of LED activation pins is simultaneously activated, corresponding to each stepped level.

FIG. 4 is a graph 400 illustrating a variable frequency pattern mirror sweep pattern in accordance with embodiments of the present invention. The horizontal axis 401 represents time. The vertical axis 403 represents frequency of an output pattern over time. In this embodiment, the output pattern 420 comprises a first section 421 and a second section 422. The first section increases from a frequency Fmin at time t0, and includes a continuous increase in frequency up to a maximum frequency Fmax at time t1. The second section 422 decreases from frequency Fmax at time t1, back to frequency Fmin at time t2. The pattern then repeats.

FIG. 5 is a graph 500 illustrating a variable frequency pattern mirror step pattern in accordance with embodiments of the present invention. The horizontal axis 501 represents time. The vertical axis 503 represents frequency of an output pattern over time. In this embodiment, the output pattern 520 comprises a first section 521 and a second section 522. First section 520 starts at a frequency Fmin at time t0, and includes a stepped increase in frequency up to a maximum frequency Fmax at time t1. While six stepped levels per sweep are shown in FIG. 3, some embodiments may have 8 stepped levels or more. In one embodiment, a first level has a fundamental frequency of 250 Hz, a second level has a fundamental frequency of 500 Hz, a third level has a fundamental frequency of 750 Hz, a fourth level has a fundamental frequency of 1000 Hz, a fifth level has a fundamental frequency of 1250 Hz, a sixth level has a fundamental frequency of 1500 Hz, a seventh level has a fundamental frequency of 1750 Hz, and an eighth level has a fundamental frequency of 2000 Hz. The process then repeats, up until time t2. The difference between time t1 and time t0 represents the sweep time interval. A second section 522 starts at time t1, and follows a "mirror" pattern of first section 520, stepping down to frequency Fmin at time t2.

FIG. 6 is a graph 600 illustrating a variable frequency pattern notched pattern in accordance with embodiments of the present invention. The notched pattern may be applied to both mirrored and non-mirrored patterns. For exemplary purposes, a mirrored pattern is shown. The notch filter establishes a first notch frequency Fn1, and a second notch frequency Fn2. During the sweep, the output of the signal generator (104 of FIG. 1) is muted when the instantaneous output frequency falls within the notch 632 defined by frequencies Fn1 and Fn2. In some cases, a patient may have particular sensitivities to a frequency range. This may sometimes occur in cases of patients having autism spectrum disorders, and/or sensory integration disorders. Hence, embodiments of the present invention allow the output signal 620 to be customized to accommodate these sensitivities. As the pattern continues beyond time t1, and the instantaneous output frequency again falls between frequencies Fn1 and Fn2, a second notch 634 is established, which again mutes the output of the signal generator. In some embodiments, Fn1 ranges from about 200 Hz to about 300 Hz, and Fn2 ranges from about 500 Hz to about 600 Hz. The activation and control of the notch filter may be configured using the NOTCH ACTIVATION, NOTCH START FREQUENCY, and NOTCH END FREQUENCY control registers. In some embodiments, the output of the signal generator (104 of FIG. 1) is not muted when the instantaneous output frequency falls within the notch 632 defined by frequencies Fn1 and Fn2, but is instead, attenuated by a predetermined amount (e.g. 6-7 dB).

FIG. 7 is an exemplary user interface for an apparatus 700 incorporating an electronic device in accordance with embodiments of the present invention. Apparatus 700 may be used to perform QRI (Quantum Reflex Integration). Apparatus 700 comprises an enclosure 728. Within the enclosure 728 is a display 738. Display 738 may be a liquid crystal display (LCD) or other suitable display. The display 738 may show various configuration options such as a predefined pattern 772, a sweep time 774, and a notch filter range 776. Apparatus 700 may further comprise navigation control 732, volume control 730, an OK button 734, and a BACK button 736. The navigation control 732, OK button 734, volume control 730, and BACK button 736 may be used to navigate menus displayed on display 738 and allow user configuration of various parameters such as pattern selection (continuous as in FIG. 2 or stepped as in FIG. 3), sweep time interval, or setting a fixed frequency output (e.g. 440 Hz). The volume of the sound may also be adjusted. Additionally, effects such as left-right panning or flanging/phase shifting may be selected. Some embodiments may have a touch screen, and all buttons may be "soft" buttons that are rendered on the touch screen. Apparatus 700 may be powered by a battery (not shown). In some embodiments, the battery may be a rechargeable battery. Other embodiments may utilize non-rechargeable batteries. Other embodiments may utilize AC power instead of, or in addition to battery power. An LED bank 740 may include one or more light emitting diodes, indicated generally as reference 742. Some embodiments may comprise eight LEDs. The LEDs may comprise a variety of colors. Some embodiments may include an infrared LED. Some embodiments may include LEDs of one or more of the following colors: red, orange, yellow, green, blue, indigo, violet, and white.

FIG. 8 is an exemplary individual light activation sequence in accordance with embodiments of the present invention. LED bank 850A shows the LEDs (852A-866A) at an initial time. LED 852A is illuminated (indicated by fill pattern), and the other LEDs (854A-866A) are not illuminated. LED bank 850B shows the LEDs (852B-866B) at a subsequent time. LED 852B is not illuminated, and LED 854B is illuminated. The illumination of the LEDs may be coordinated with the output pattern. For example, for each step in FIG. 3, a new LED may be illuminated, and the previous LED set to an off state. LED bank 850C shows the LEDs (852B-866B) at a subsequent time. LED 854C is not illuminated, and LED 855C is illuminated. LED bank 850D shows the LEDs (852B-866B) at a subsequent time. LED 855D is not illuminated, and LED 856D is illuminated. The sequence continues with a single LED being illuminated at any given time.

FIG. 9 is an exemplary accumulative light activation sequence in accordance with embodiments of the present invention. LED bank 950A shows the LEDs (952A-966A) at an initial time. LED 952A is illuminated (indicated by fill pattern), and the other LEDs (954A-966A) are not illuminated. LED bank 950B shows the LEDs (952B-966B) at a subsequent time. Both LED 952B and LED 954B are illuminated. LED bank 950C shows the LEDs (952C-966C) at a subsequent time. Now three LEDs, (952C, 954C, and 955C) are illuminated. LED bank 950D shows the LEDs (952D-966D) at a subsequent time. Now four LEDs, (952D, 954D, 955D, and 956D) are illuminated. The process may continue until all LEDs are illuminated. Then the process may repeat where all LEDs are set to off, and the process of activating the LEDs continues again. The sequence of LED activation (controlled by LED activation pins 124) may be coordinated to the output of signal generator (104 of FIG. 1).

FIG. 10 is an exemplary group light activation sequence in accordance with embodiments of the present invention. LED bank 1050A shows the LEDs (1052A-1066A) at an initial time. LED 1052A is illuminated (indicated by fill pattern), and the other LEDs (1054A-1066A) are not illuminated. LED bank 1050B shows the LEDs (1052B-1066B) at a subsequent time. Both LED 1052B and LED 1054B are illuminated. LED bank 1050C shows the LEDs (1052C-1066C) at a subsequent time. Now three LEDs, (1052C, 1054C, and 1055C) are illuminated. LED bank 1050D shows the LEDs (1052D-1066D) at a subsequent time. Now the pattern of the three LEDs has shifted such that LED 1052D is not illuminated, and LEDs 1054D, 1055D, and 1056D are illuminated. The group light activation may continue to travel along the bank of LEDs, and may be coordinated or synchronized with the output pattern.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, circuits, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. An apparatus for generating multiple simultaneous electronic signals, comprising:
   a signal generator;
   a non-transitory memory;
   a processor configured and disposed to access the non-transitory memory;
   a plurality of laser activation pins;
   a plurality of light emitting diode (LED) activation pins;
   a plurality of light emitting diodes configured and disposed to be controlled by the plurality of light emitting diode (LED) activation pins;
   wherein the non-transitory memory contains instructions, that when executed by the processor programs a plurality of control registers to configure the signal generator to generate a variable frequency pattern on a first output of the signal generator, and wherein the variable frequency pattern comprises a notched pattern and wherein the processor comprises a plurality of control registers, wherein the plurality of control registers includes a notch activation control register configured and disposed to enable a notch filter, a notch start frequency control register configured and disposed to set a starting frequency for the notch filter, and a notch end frequency control register configured and disposed to set an ending frequency for the notch filter; wherein the variable frequency pattern comprises a step pattern comprising a plurality of stepped levels, and wherein the plurality of stepped levels includes a first stepped level at a fundamental frequency of 250 Hz, a second stepped level at a fundamental frequency of 500 Hz, a third stepped level at a fundamental frequency of 750 Hz, a fourth stepped level at a fundamental frequency of 1000 Hz, a fifth stepped level at a fundamental frequency of 1250 Hz, a sixth stepped level at a fundamental frequency of 1500 Hz, a seventh stepped level at a fundamental frequency of 1750 Hz, and an eighth stepped level at a fundamental frequency of 2000 Hz, and wherein the non-transitory memory further contains instructions, that when executed by the processor program a plurality of control registers to activate a different subset of the plurality of LED activation pins corresponding to each stepped level of the plurality of stepped levels.

2. The apparatus of claim 1, wherein the variable frequency pattern comprises a mirror step pattern.

3. An apparatus for generating multiple simultaneous electronic signals, comprising:
   a signal generator;
   a non-transitory memory;
   a processor configured and disposed to access the non-transitory memory;
   a plurality of laser activation pins;
   a plurality of light emitting diode (LED) activation pins;
   wherein the non-transitory memory contains instruction, that when executed by the processor, programs a plurality of control registers to configure the signal generator to generate a first variable frequency pattern on a first output of the signal generator, and a second variable frequency pattern on a second output of the signal generator, and wherein the plurality of control registers includes a notch activation control register configured and disposed to enable a notch filter, a notch start frequency control register configured and disposed to set a starting frequency for the notch filter, and a notch end frequency control register configured and disposed to set an ending frequency for the notch filter;
   wherein the first variable frequency pattern comprises a step pattern comprising a plurality of stepped levels, and wherein the plurality of stepped levels includes a first stepped level at a fundamental frequency of 250 Hz, a second stepped level at a fundamental frequency of 500 Hz, a third stepped level at a fundamental frequency of 750 Hz, a fourth stepped level at a fundamental frequency of 1000 Hz, a fifth stepped level at a fundamental frequency of 1250 Hz, a sixth stepped level at a fundamental frequency of 1500 Hz, a seventh stepped level at a fundamental frequency of 1750 Hz, and an eighth stepped level at a fundamental frequency of 2000 Hz, and wherein the non-transitory memory further contains instructions, that when executed by the processor program a plurality of control registers to activate a different subset of the plurality of LED activation pins corresponding to each stepped level of the plurality of stepped levels; and
   wherein the second variable frequency pattern is a time-delayed version of the first variable frequency pattern.

4. The apparatus of claim 3, wherein the second variable frequency pattern is time-delayed by a time interval ranging from 200 milliseconds to 300 milliseconds.

5. The apparatus of claim 3, wherein the second variable frequency pattern is 180 degrees out of phase from the first variable frequency pattern.

6. The apparatus of claim 3, wherein the first variable frequency pattern and the second variable frequency pattern comprises a mirror step pattern.

7. A method for generating multiple simultaneous electronic therapeutic signals, comprising:
generating a first variable frequency pattern on a first signal output;
activating one or more laser activation pins based on an instantaneous state of the variable frequency pattern;
providing a processor and non-transitory memory containing instructions; and
activating one or more light emitting diode (LED) activation pins based on the instantaneous state of the variable frequency pattern, and programming a notch start frequency control register with a starting frequency for a notch filter, and programming a notch end frequency control register with an ending frequency for the notch filter,
wherein the variable frequency pattern comprises a step pattern comprising a plurality of stepped levels, and wherein the plurality of stepped levels includes a first stepped level at a fundamental frequency of 250 Hz, a second stepped level at a fundamental frequency of 500 Hz, a third stepped level at a fundamental frequency of 750 Hz, a fourth stepped level at a fundamental frequency of 1000 Hz, a fifth stepped level at a fundamental frequency of 1250 Hz, a sixth stepped level at a fundamental frequency of 1500 Hz, a seventh stepped level at a fundamental frequency of 1750 Hz, and an eighth stepped level at a fundamental frequency of 2000 Hz, and
wherein the non-transitory memory further contains instructions, that when executed by the processor, programs a plurality of control registers to activate a different subset of the plurality of LED activation pins corresponding to each stepped level of the plurality of stepped levels; and,
muting the first signal output when the first variable frequency pattern has a frequency that is between the starting frequency and the ending frequency.

8. The method of claim 7, wherein generating a first variable frequency pattern comprises generating a mirror step pattern.

9. The method of claim 7, further comprising generating a second variable frequency pattern on a second signal output.

10. The method of claim 9, wherein generating a second variable frequency pattern comprises generating a variable frequency pattern that is 180 degrees out of phase with the first variable frequency pattern.

* * * * *